United States Patent
Grant et al.

(10) Patent No.: US 10,780,289 B2
(45) Date of Patent: *Sep. 22, 2020

(54) WAVEFORM ENERGY INFLUENCE OF OBJECTS USING FEEDBACK CONTROL

(71) Applicant: STRATHSPEY CROWN HOLDINGS, LLC, Newport Beach, CA (US)

(72) Inventors: Robert Edward Grant, Laguna Beach, CA (US); Matthew T. Case, Laguna Hills, CA (US); Todd Mirzai, Honolulu, HI (US)

(73) Assignee: Strathspey Crown Holdings, LLC, Newport Beach, CA (US)

(*) Notice: Subject to any disclaimer, the term of this patent is extended or adjusted under 35 U.S.C. 154(b) by 103 days.

This patent is subject to a terminal disclaimer.

(21) Appl. No.: 14/710,275

(22) Filed: May 12, 2015

(65) Prior Publication Data
US 2016/0331988 A1 Nov. 17, 2016

(51) Int. Cl.
*A61N 1/40* (2006.01)
*A61B 90/00* (2016.01)
(Continued)

(52) U.S. Cl.
CPC .............. *A61N 1/40* (2013.01); *A61B 90/37* (2016.02); *A61N 7/02* (2013.01); *A61B 5/0066* (2013.01);
(Continued)

(58) Field of Classification Search
CPC ....... A61B 5/037; A61B 5/0066; A61B 5/055; A61N 7/00
See application file for complete search history.

(56) References Cited

U.S. PATENT DOCUMENTS

| 6,024,690 A | 2/2000 | Lee et al. |
| 6,033,357 A | 3/2000 | Ciezki et al. |

(Continued)

FOREIGN PATENT DOCUMENTS

| CA | 2879996 A1 | 1/2014 |

OTHER PUBLICATIONS

Zimmerman et al., "Targeted treatment of cancer with radiofrequency electromagnetic fields amplitude-modulated at tumor-specific frequencies". Chinese Journal of Cancer. 2013; vol. 32, Issue 11, pp. 573-581.*

(Continued)

*Primary Examiner* — Katherine L Fernandez
*Assistant Examiner* — Yi-Shan Yang
(74) *Attorney, Agent, or Firm* — Fish IP Law, LLP

(57) ABSTRACT

A control system for delivering energy waveform radiation to influence in vivo tissue is described. For the system, the energy waveform radiation is generated by a radiation unit and is directed along a pathway to the tissue and a registration unit is provided to identify a start place relative to the in vivo tissue. Also, a monitor is provided to compare the start place with a base reference to measure an error signal between the start place and base reference. With this measured error signal, a controller operates the radiation unit using input from the monitor to effectively attain and maintain a zero error signal. More specifically, the controller can provide operational parameter inputs to the radiation unit for configuring the waveform radiation including a radiation frequency, f, and a volume intensity level, v, for the radiation and an exposure time interval, $t_i$.

13 Claims, 3 Drawing Sheets

(51) Int. Cl.
*A61N 7/02* (2006.01)
*A61B 5/00* (2006.01)
*A61B 5/055* (2006.01)
*A61N 7/00* (2006.01)

(52) U.S. Cl.
CPC ......... *A61B 5/055* (2013.01); *A61B 2090/374* (2016.02); *A61B 2090/3735* (2016.02); *A61B 2090/3762* (2016.02); *A61N 2007/0065* (2013.01)

(56) References Cited

U.S. PATENT DOCUMENTS

| | | | |
|---|---|---|---|
| 6,077,213 | A | 6/2000 | Ciezki et al. |
| 6,221,094 | B1 | 4/2001 | Bare |
| 6,309,339 | B1 | 10/2001 | Ciezki et al. |
| 6,626,816 | B1 | 9/2003 | Ciezki et al. |
| 6,725,081 | B2 | 4/2004 | Ciezki et al. |
| 7,280,874 | B2 | 10/2007 | Boehm |
| 7,418,294 | B2 | 8/2008 | May |
| 7,500,956 | B1 | 3/2009 | Wilk |
| 8,057,408 | B2 * | 11/2011 | Cain ................ A61B 17/22004 601/2 |
| 8,326,408 | B2 | 12/2012 | Green et al. |
| 8,440,154 | B2 | 5/2013 | Fahs, II et al. |
| 8,591,419 | B2 | 11/2013 | Tyler |
| 2007/0106157 | A1 * | 5/2007 | Kaczkowski .......... A61B 5/015 600/438 |
| 2007/0123780 | A1 | 5/2007 | Wu |
| 2007/0128590 | A1 * | 6/2007 | Boehm ................. C12N 13/00 435/6.12 |
| 2012/0059243 | A1 * | 3/2012 | Vortman ................. A61N 7/02 600/411 |
| 2012/0130287 | A1 * | 5/2012 | Gruber ..................... A61N 7/00 601/2 |
| 2012/0215106 | A1 * | 8/2012 | Sverdlik ............... A61M 31/00 600/439 |
| 2013/0023715 | A1 * | 1/2013 | Raleigh ................ A61N 5/1037 600/1 |
| 2013/0269441 | A1 * | 10/2013 | Doyle .................... G01N 29/07 73/598 |
| 2014/0276055 | A1 * | 9/2014 | Barthe ..................... A61N 7/02 600/439 |
| 2014/0303525 | A1 * | 10/2014 | Sitharaman ............. A61N 7/00 601/2 |
| 2015/0080990 | A1 * | 3/2015 | Crunick ................... A61D 1/00 607/101 |
| 2015/0165091 | A1 * | 6/2015 | Dalecki ............... A61L 27/3804 424/444 |
| 2016/0023019 | A1 * | 1/2016 | Filiberti ............... A61N 5/1075 600/1 |

OTHER PUBLICATIONS

Qi et al., "Resonant acoustic radiation force optical coherence elastography". Applied Physics Letters 2013, 103(10), 103704.*
NIH Stem Cell Information Home Page. In Stem Cell Information [https://stemcells.nih.gov/info/basics/2.htnn]. Bethesda , MD: National Institutes of Health, U.S. Department of Health and Human Services, 2016 (Year: 2016).*
John et al., "Developmental epigenetics: phenotype and the flexible epigenome". Frontiers in Cell and Developmental Biology, Oct. 2018, vol. 6, Article 130, pp. 1-4. (Year: 2018).*
Boland et al., "Epigenetic regulation of pluripotency and differentiation". Circ. Res. 2014; 115(2): 311-324. (Year: 2014).*
PCT International Search Report, Application No. PCT/US2016/029506, dated Apr. 27, 2016.

* cited by examiner

WAVEFORM ENERGY INFLUENCE OF OBJECTS USING FEEDBACK CONTROL

FIELD OF THE INVENTION

The present invention pertains generally to systems and methods for influencing objects using waveform energy. More particularly, the present invention pertains to systems and methods for influencing cellular structures to morph or transition into a target value or condition, by applying waveform energy to the structures. The present invention is particularly, but not exclusively, useful for influencing objects by applying waveform energy to them while controlling the process using a feedback control system.

BACKGROUND OF THE INVENTION

Feedback can be used to make adjustments to one or more system inputs, to thereby drive a system output toward a target value or condition. In this process, information output by the system is used to determine the appropriate system input adjustments. In some instances, an ability to understand the relationship between output information and one or more input adjustments can allow a process to be developed that achieves results that are otherwise unobtainable using uncontrolled or so-called "open-loop" type systems.

One process in which feedback can be advantageously used involves the exposure of tissue to waveform energy. In this regard, it is known that exposing tissue to waveform energy can cause permanent changes to the tissue. In particular, it has been recognized that sonic waves and other electromagnetic waves can be employed to cause transformative or morphological changes in cellular structure. Not surprisingly, many of these changes may be very beneficial. Thus, within the medical community there is increasing interest insofar as the extent to which such changes may be employed to beneficially alter the functionality of a cellular structure.

From a mechanical perspective, each individual cellular structure (tissue cell) has a natural frequency at which it will oscillate (i.e. vibrate) when subjected to an external force. Another consequence of this natural frequency is that cellular structures will respond to periodically applied external forces having certain frequencies, such as the natural frequency, quite differently than they will respond to external forces having other applied frequencies.

From a biological perspective, each cell type (e.g. a liver cell) will have observable characteristics which naturally result from the cell's environment. A set of these observable characteristics is generally referred to as a phenotype. Further, it is known that the set of characteristics for a defined phenotype of a cellular structure can be epigenetically influenced by externally applied forces. Moreover, this can happen regardless of whether the cellular structure is influenced in vivo or in vitro.

In light of the above, it is an object of the present invention to provide efficient systems and methods for influencing cellular structures when waveform energy is applied to the structures. It is another object of the present invention to provide a system and method for directing waveform energy to an object which utilizes closed-loop feedback control to obtain an improved interaction between the waveform energy and the object. It is yet another object of the present invention to apply waveform energy to tissue under feedback control to epigenetically influence tissue cells, and to thereby alter the functionality of an in vivo, or an in vitro, target tissue. Yet another object of the present invention is to provide a system and method for waveform energy influence of objects using feedback control which is easy to use and commercially cost effective.

SUMMARY OF THE INVENTION

In accordance with the present invention, a control system for delivering energy waveform radiation to influence in vivo tissue includes a radiation unit. In particular, the energy waveform radiation that is generated by the radiation unit is directed along a beam pathway toward the tissue. For the present invention, a registration unit is provided to identify a start place relative to the in vivo tissue, to establish where the radiation is to be directed.

A monitor is provided for the control system to compare the start place vis-a'-vis a base reference. This is done by measuring an error signal between the start place and the base reference. With this error signal measured by the monitor, a controller in the system operates the radiation unit to effectively attain and maintain a zero error signal. More specifically, the controller can adjust the beam pathway and/or provide operational parameter inputs to the radiation unit for configuring the waveform radiation. For example, these operational parameter inputs can include a radiation frequency, f, a volume intensity level for the radiation, v, and an exposure time interval, $t_1$. When pulsed radiation is employed, an additional operational parameter can be input to the radiation unit, namely, the pulse duration, $t_d$, can be specified by the controller. In some implementations, a computer is used for coordinating respective operations of the radiation unit, the monitor, and the controller.

In a first embodiment of the present invention, the control system includes an imaging unit for creating an image of the in vivo tissue to be radiated. For example, the imaging unit can be an Optical Coherence Tomography (OCT) imaging unit, a Magnetic Resonance Imaging (MRI) imaging unit, a Positron Emission Tomography (PET) imaging unit or a Computerized Axial Tomography (CAT) imaging unit. For this embodiment, the registration unit identifies a start place relative to the in vivo tissue in the image. For instance, the start place can be a point where a focused beam of the energy waveform radiation intercepts the in vivo tissue. In the event, the monitor is connected with the imaging unit to compare the start place with the base reference, such as a target point identified on the image of the in vivo tissue. The distance between the start place and base reference is then measured and used as an error signal to control the operational parameters of the radiation unit. In one implementation, the target point is periodically repositioned on the image of the in vivo tissue. In some cases, the target tissue is moved in a pattern relative to the in vivo tissue in accordance with a selected protocol.

In another embodiment of the present invention, the base reference is a predefined phenotype for the in vivo tissue, and the start place is a cellular structure of the in vivo tissue. For this embodiment, the monitor can be an appropriate sensor for obtaining a set of observable characteristics of the tissue to determine the required phenotype. Alternatively, this monitoring function can be performed by the periodic performance of a biopsy. In the event, management and control of the protocol by the computer is terminated when the phenotypic response corresponds with the desired phenotype.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
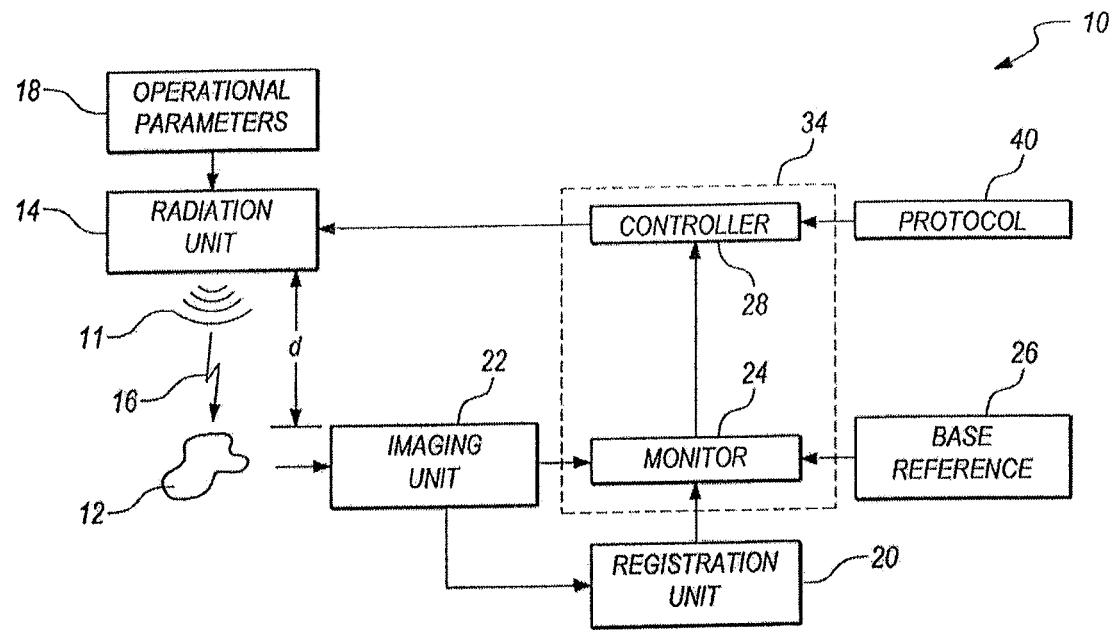
FIG. 1 is a schematic of the combination of interactive components for a system in accordance with the present invention.

In accordance with the present invention, a control system 10 for delivering an energy waveform radiation 11 to influence in vivo tissue 12 includes a radiation unit 14. As shown, the energy waveform radiation 11 is generated by the radiation unit 14 and is directed along a pathway 16 to the tissue 12. FIG. 1 also shows that the radiation unit 14 will be positioned at a distance, d, from the target tissue 12. Typically, the distance d will be greater than about 10 millimeters (d>10 mm).

For the system 10 shown in FIG. 1, the energy waveform radiation 11 may be focused or unfocused and may be pulsed or continuous. The radiation 11 can be directed onto exposed tissue 12 to influence the exposed tissue 12, or the radiation 11 can be directed to pass through surface tissue to a subsurface location for the purpose of influencing tissue 12 located below the surface. As contemplated for the present invention, both soft tissues and hard tissues may be influenced using the systems and methods described herein.

As envisioned for the present invention, the radiation 11 to be employed for influencing target tissue 12 may be of any waveform energy known in the art. It may be radiation in the electromagnetic spectrum. For many instances, however, the radiation will be between wavelengths of $10^{-25}$m to $10^3$ m. It may also be periodic mechanical vibrations. In this latter case, the radiation 11 may be acoustic sound waves in the range between 20 Hz and 20 kHz, and may also include infrasound waves (<20 Hz) and ultrasound waves (>20 kHz). Further, the tone of the radiation 11 may be either pure (single frequency) or complex (multi-frequency).

FIG. 1 shows that the radiation unit 14 receives operational parameters 18 as an input. These operational parameters 18 can include a radiation frequency, f, a volume intensity level for the radiation, v, and an exposure time interval, $t_i$. When pulsed radiation 11 is employed, an additional operational parameter 18 can be input to the radiation unit 14, namely, the pulse duration, $t_d$, can be specified by the controller 28.

Continuing now with reference to FIG. 1, it can be seen for the present invention that a registration unit 20 is provided which receives an image of the tissue 12 that is generated by an imaging unit 22. One purpose here is to identify a start place 30 relative to the in vivo tissue 12 (see FIG. 2). The registration unit 20 then outputs the start place 30 to a monitor 24. In this operation, the imaging unit 22 can be an Optical Coherence Tomography (OCT) imaging unit, a Magnetic Resonance Imaging (MRI) imaging unit, a Positron Emission Tomography (PET) imaging unit or a Computerized Axial Tomography (CAT) imaging unit.

During an operation of the system 10, it is to be appreciated that the energy waveform radiation 11 which is generated by the radiation unit 14 will be controlled by a computer 34. As envisioned for the present invention, this control will be accomplished using closed-loop feedback control techniques. In overview, FIG. 2 depicts the functional aspects of a control circuit 19 for such an operation.

Figure 2:
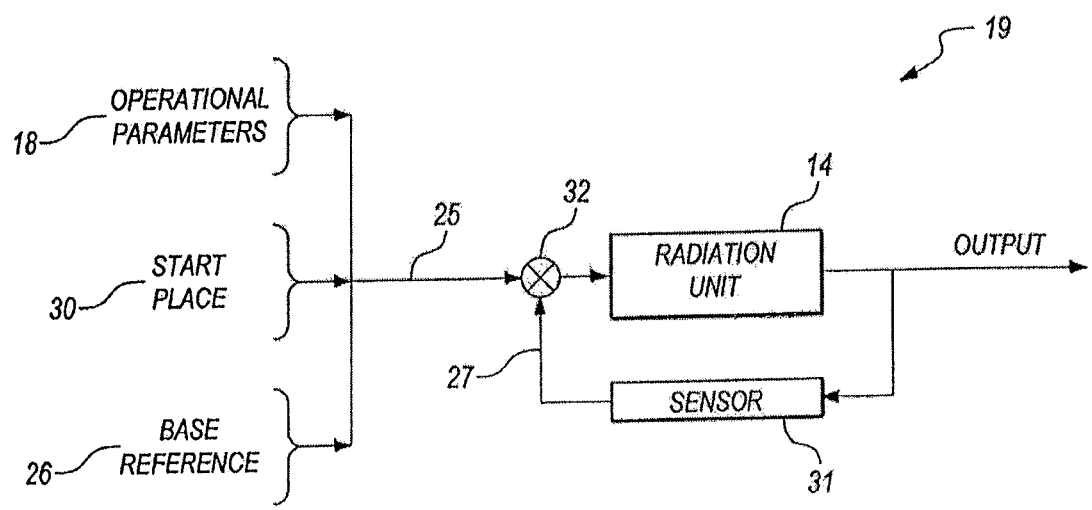
FIG. 2 is a functional presentation of components for closed-loop control of a radiation unit in the system of the present invention.

With reference to FIG. 2 it will be seen that several different considerations contribute to the identification of an appropriate input 25 for the circuit 19 and its closed-loop control of the system 10. As indicated in FIG. 2, a selected combination of these considerations will determine values for the operational parameters 18 (f, v, and $t_i$) that are necessary for the radiation unit 14 to generate an effective energy waveform radiation 11. Depending on the particular protocol 40 that is to be followed, the input 25 will also include the determination of a start place 30 and a base reference 26. Further, a sensor 31 needs to be employed to provide the necessary feedback information for closed-loop feedback control. The particular type of sensor 31 that is required will essentially depend on the operational requirements of the protocol 40 that is to be followed. In turn, all of this depends on the objective(s) to be gained by an operation of the system 10.

For one embodiment of the present invention, the objective(s) of protocol 40 may be to improve the vitality, or alter the functionality of the target tissue 12. This will likely include a proper identification, and an accurate location, of the target tissue 12 for treatment. In this case, the input 25 will necessarily include information regarding the start place 30 (e.g. location), to where the waveform energy radiation 11 is to be directed. It may also need to include a base reference 26 for accurately and appropriately maintaining the start place 30' (see FIG. 3A). For this purpose, the sensor 31 will most likely be an imaging unit 22 of a type as disclosed above.

Figure 3A:
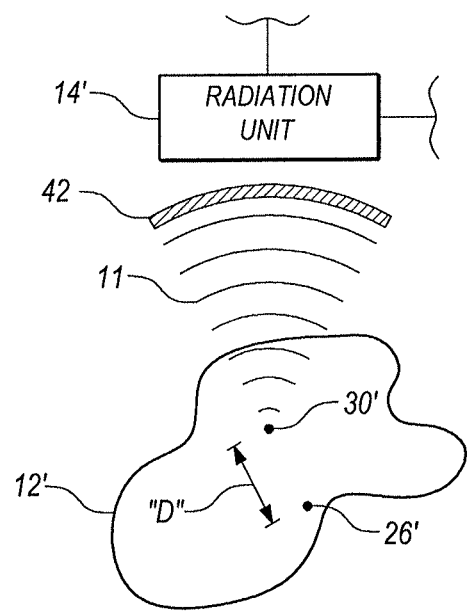
FIG. 3A is a schematic of a portion of a system in accordance with the present invention illustrating a start point and a target point (baseline reference)
Figure 3B:
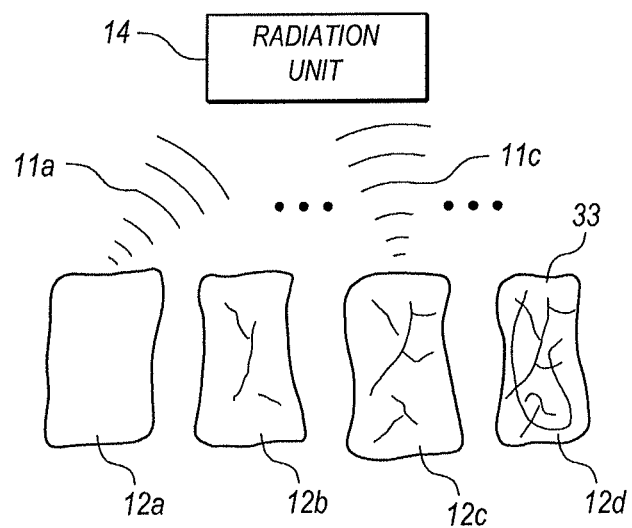
FIG. 3B is a schematic of a transformative or morphological change in the target tissue during an operation of the present invention.

For another embodiment of the present invention, the objective of protocol 40 may be to morph an undifferentiated target tissue 12 (e.g. target tissue 12a in FIG. 3B) into a desired phenotype 33 (e.g. target tissue 12d in FIG. 3B). More specifically, FIG. 3B shows a sequence of morphed target tissues 12 during such a transformation (Note: the target tissues 12a, 12b, 12c, and 12d shown here are only exemplary). Moreover, for this example, as part of this sequence radiation 11a is influencing target tissue 12a. Similarly, radiation 11c is shown influencing target tissue 12c. In a procedure such as this, the input 25 will necessarily include information of the desired phenotype 33 (i.e. target tissue 12d) that is to be created during the procedure. To do this, an accurate description of the desired phenotype 33 is necessarily used as the base reference 26. As envisioned for this embodiment of the present invention, the sensor 31 may well be a sequence of biopsy procedures which are periodically performed to titrate the target tissue 12.

In accordance with a protocol 40 for either of the above embodiments, closed-loop feedback control is provided by first establishing the necessary input 25 for an operation of the radiation unit 14. Specifically, this input 25 (e.g. f, v, $t_i$, start place 30 and base reference 26) is provided to the computer 34 for controlling and operating the radiation unit 14. It is in accordance with the input 25 that the radiation unit 14 is activated to generate the waveform energy radiation 11. During the protocol 40, sensor 31 records the influence of this radiation 11 on the target tissue 12. Then, based on the progress of this influence, a feedback signal 27 is generated which is forwarded to the summing point 32. At the summing point 32, the feedback signal 27 is added to the input 25 to thereby generate an error signal that will appropriately adjust the operation of radiation unit 14 to maintain its operational efficacy.

In further detail, and by referring back to FIG. 1, it can be seen that the controller 28 of computer 34 receives an operational protocol 40 together with other operational information from the monitor 24. With these inputs, the controller 28 operates the radiation unit 14. More specifically, the controller 28 can adjust the beam pathway 16 and/or modify the operational parameter inputs 18 to the radiation unit 14 for configuring the waveform radiation 11. Suitable protocols for influencing tissue to obtain a selected tissue response can be found in co-pending, co-owned U.S. patent application Ser. No. 14/488,101, filed Sep. 16, 2014 and titled "System and Method for Sonic Radiation for Influencing Cellular Structures," the entire contents of which are hereby incorporated by reference herein.

As implied above with reference to FIG. 3A, an embodiment of the present invention which requires directional control over the waveform energy radiation 11 will preferably include a parabolic speaker 42 which is affixed to the radiation unit 14'. Specifically, speaker 42 can be employed to project a focused beam of the radiation 11 in the form of acoustic sound waves to the tissue 12'. As shown in FIG. 3A, the radiation 11 is directed to a focal spot at the start place 30' in the tissue 12'. The monitor 24 (see FIG. 1) compares information regarding the start place 30' (focal spot), as received from the imaging unit 22, with the base reference 26' (i.e. a target point identified on the image of the in vivo tissue). The distance, D, shown in FIG. 3A between the start place 30' and base reference 26' is then measured as an error signal and used by the controller 28 to adjust the radiation unit 14', and for directional control of the radiation 11. In one implementation, the base reference 26' (i.e. target point) is periodically repositioned on the image of the in vivo tissue 12'. In some cases, the base reference 26' (i.e. target tissue) is moved in a pattern relative to the in vivo tissue 12' in accordance with a selected protocol (e.g. protocol 40 shown in FIG. 1).

Figure 4:
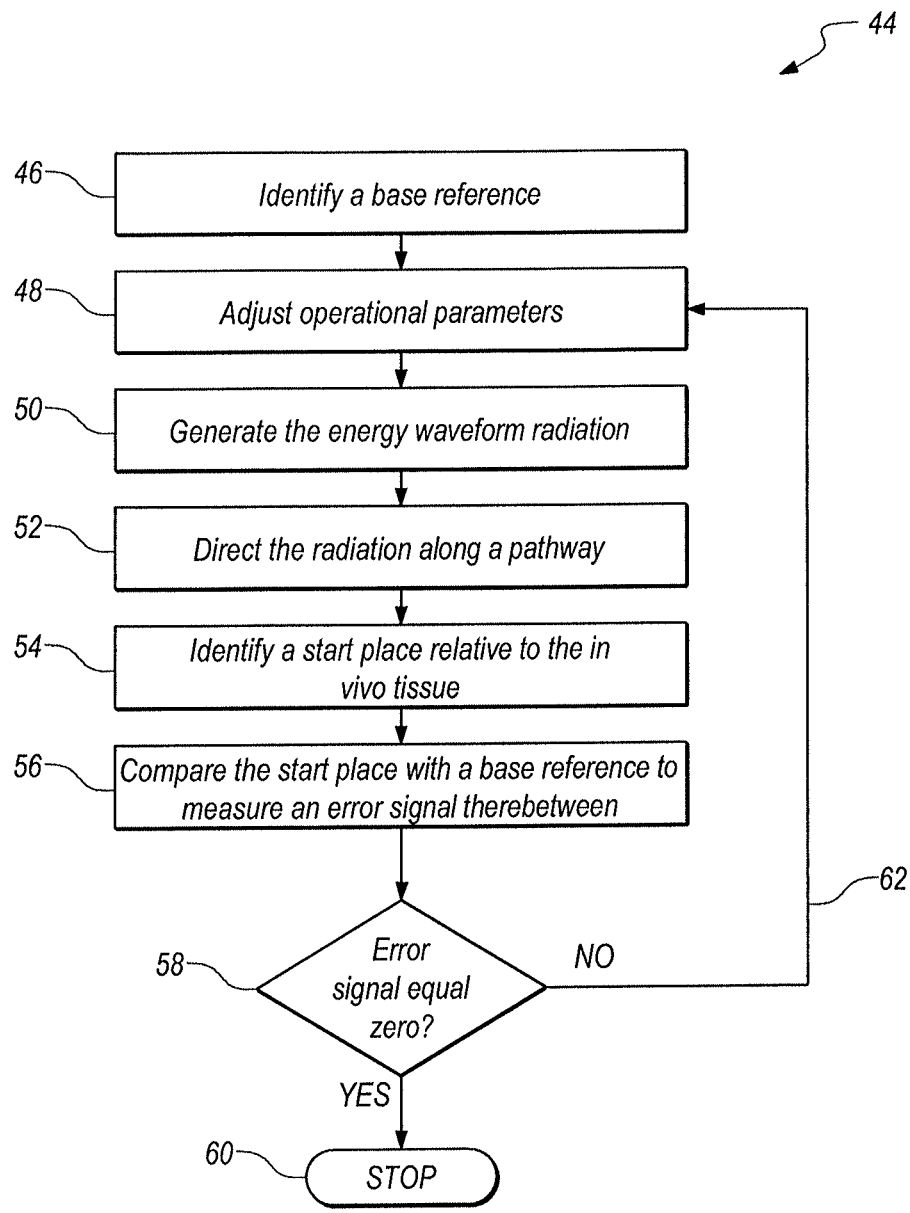
FIG. 4 is an operational flowchart showing an implementation in accordance with the present invention.

FIG. 4 illustrates a procedure 44 for influencing in vivo tissue 12 using feedback control. As shown, the procedure 44 begins by identifying a base reference 26 (block 46) for the in vivo tissue. For the present methods, this base reference 26 is either a start place 30 on the target tissue 12 or a predefined phenotype 33 for the in vivo tissue. For example, the objective of the procedure 44 may be the creation of a particular type of stem cell (e.g. liver cell depicted as target tissue 12d in FIG. 3B) from an otherwise undefined or undifferentiated cell (e.g. target tissue 12a in FIG. 3B). In this case, the desired phenotype 33 (outcome) will be defined to have the requisite characteristics of the particular type stem cell that is desired (e.g. liver cell). As another example, the objective of a protocol 40 may be to terminate the viability of a cellular structure, such as by killing cancer cells. Still another example may be to assert directional control over the radiation unit 14' (see FIG. 3A).

With the base reference 26 identified, the next step is to adjust the operational parameters 18 (box 48) for the radiation unit 14, 14' (see FIGS. 1, 3A and 3B). As indicated above, the operational parameters 18 can include, but are not necessarily limited to, the radiation frequency, f, volume intensity level, v, for the radiation exposure time interval, $t_i$, and when pulsed radiation is employed, the pulse duration, $t_d$. Once the operational parameters 18 have been initialized, the next step is to generate the energy waveform radiation 11 (box 50) and direct it toward the targeted tissue 12 (box 52). After an initial exposure of the in vivo target tissue 12 to the radiation 11, the next step is to identify a start place relative to the in vivo tissue 12 (box 54). For example, this can be performed by imaging the tissue 12 in situ, by using a sensor 31 (e.g. imaging unit 22), or by performing a biopsy on a portion of the tissue 12. Next, box 56 indicates that the start place 30 is compared with a base reference 26 to measure an error signal therebetween. If the error signal equals zero (i.e. if the predefined phenotype 33 has been achieved) (box 58) then the procedure is complete (box 60). Otherwise, as indicated by arrow 62, boxes 48, 50, 52, 54 and 56 are repeated. This process is repeated until the error signal is zero (box 58) and the predefined phenotype 33 has been achieved.

While the particular embodiments and implementation of Waveform Energy Influence of Objects Using Feedback Control as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method of differentiating an undifferentiated cell into a particular type of cell having a desired phenotype, using closed-loop feedback control, the method comprising steps of:

establishing an input signal for an operation of a radiation unit;

generating a focused beam of a radiation having a frequency in accordance with the input signal; directing the focused beam to the undifferentiated cell;

using a sensor to measure a progress of the differentiating of the undifferentiated cell, wherein the step of using the sensor to measure the progress comprises using the sensor to obtain a set of observable characteristics of the undifferentiated cell;

generating a comparison between the set of observable characteristics of the undifferentiated cell and the desired phenotype;

generating a feedback signal based on the comparison;

generating an error signal by adding the feedback signal to the input signal;

adjusting an operational parameter of the focused beam in response to the error signal; and terminating the radiation if the error signal equals zero, wherein the desired phenotype is a liver cell phenotype or a cancer-free cell phenotype.

2. The method as recited in claim 1, further comprising directing the focused beam along a pathway using a parabolic speaker.

3. The method as recited in claim 1 wherein the focused beam includes at least one of infrasound waves and ultrasound waves.

4. The method as recited in claim 1, wherein the focused beam is pulsed.

5. The method as recited in claim 1, wherein the frequency is equal to or near a natural frequency of the desired phenotype.

6. The method as recited in claim 1, wherein the operational parameter is selected from a group consisting of a radiation frequency, volume intensity level, and exposure time interval.

7. The method as recited in claim 1, wherein the step of using the sensor to obtain the set of observable characteristics of the undifferentiated cell comprises using an imaging unit to generate an image of the undifferentiated cell and comparing the image with an image of the desired phenotype.

8. A method for epigenetically influencing a cellular structure in a target tissue in a patient into a desired phenotype using closed-loop feedback control, comprising steps of:
  defining the desired phenotype for the target tissue, wherein the desired phenotype includes a target cellular structure having a natural frequency;
  establishing an input signal for an operation of a radiation unit to generate waveform energy having the natural frequency equal to or near a natural frequency of the target tissue;
  radiating the target tissue with the waveform energy in accordance with the input signal, wherein the radiation with the waveform energy is accomplished in accordance with a predetermined protocol to epigenetically influence the target tissue;
  using a sensor to measure a progress of the epigenetic influence to the cellular structure in the target tissue, wherein the step of using the sensor to measure the progress of the epigenetic influence comprises using the sensor to obtain a set of observable characteristics of the target tissue and comparing the set of observable characteristics with the desired phenotype;
  generating a feedback signal based on the measured progress of the epigenetic influence;
  generating an error signal by adding the feedback signal to the input signal;
  adjusting an operational parameter of the waveform energy in response to the error signal; and
  terminating application of the predetermined protocol when the error signal is zero,
  wherein the desired phenotype is a liver cell phenotype or a cancer-free cell phenotype.

9. The method as recited in claim 8, wherein the operational parameter is selected from a group consisting of a radiation frequency, volume intensity level, and exposure time interval.

10. The method as recited in claim 8, wherein the using of the sensor to obtain a set of observable characteristics of the target tissue and the comparing the set of observable characteristics with the desired phenotype comprises using an imaging unit to generate an image of the cellular tissue and comparing the image of the cellular structure with an image of the desired phenotype.

11. The method as recited in claim 10, wherein the imaging unit is selected from a group consisting of an Optical Coherence Tomography (OCT) imaging unit, a Magnetic Resonance Imaging (MRI) imaging unit, a Positron Emission Tomography (PET) imaging unit and a Computerized Axial Tomography (CAT) imaging unit.

12. The method as recited in claim 8, wherein the measurement of the progress comprises measuring a difference between the cellular structure and the desired phenotype.

13. A method for epigenetically influencing a cellular structure in a target tissue in a patient into a desired phenotype using closed-loop feedback control, comprising steps of:
  defining the desired phenotype for the target tissue, wherein the desired phenotype includes a target cellular structure having a natural frequency;
  establishing an input signal for an operation of a radiation unit to generate waveform energy having the natural frequency equal to or near a natural frequency of the target tissue;
  radiating the target tissue with the waveform energy in accordance with the input signal, wherein the radiation with the waveform energy is accomplished in accordance with a predetermined protocol to epigenetically influence the target tissue;
  using a sensor to measure a progress of the epigenetic influence to the cellular structure in the target tissue, wherein the step of using the sensor to measure the progress of the epigenetic influence comprises periodically performing a sequence of biopsy procedures on the target tissue;
  generating a feedback signal based on the measured progress of the epigenetic influence;
  generating an error signal by adding the feedback signal to the input signal;
  adjusting an operational parameter of the waveform energy in response to the error signal; and
  terminating application of the predetermined protocol when the error signal is zero,
  wherein the desired phenotype is a liver cell phenotype or a cancer-free cell phenotype.

* * * * *